(12) United States Patent
Kim

(10) Patent No.: US 10,010,317 B2
(45) Date of Patent: Jul. 3, 2018

(54) METHOD OF IMPROVING ELASTICITY OF TISSUE OF LIVING BODY

(71) Applicant: Young Jae Kim, Seoul (KR)

(72) Inventor: Young Jae Kim, Seoul (KR)

(*) Notice: Subject to any disclaimer, the term of this patent is extended or adjusted under 35 U.S.C. 154(b) by 379 days.

(21) Appl. No.: 13/706,108

(22) Filed: Dec. 5, 2012

(65) Prior Publication Data

US 2014/0155913 A1   Jun. 5, 2014

(51) Int. Cl.
*A61B 17/04* (2006.01)
*A61B 17/06* (2006.01)
*A61B 17/00* (2006.01)

(52) U.S. Cl.
CPC ...... *A61B 17/0469* (2013.01); *A61B 17/0482* (2013.01); *A61B 17/06166* (2013.01); *A61B 2017/00792* (2013.01); *A61B 2017/06042* (2013.01); *A61B 2017/06052* (2013.01); *A61B 2017/06176* (2013.01)

(58) Field of Classification Search
CPC .......... A61B 17/06166; A61B 17/0401; A61B 2017/0496; A61B 2017/0412; A61B 2017/0427; A61B 2017/0458; A61B 2017/0445; A61B 2017/06171; A61B 2017/0618; A61B 2017/06185; A61B 2017/06176; A61B 2017/00792; A61B 2017/00796; A61B 2017/06052; A61B 17/0482; A61B 17/0469; A45D 44/22
USPC .................... 606/138–150, 228–232, 204.35
See application file for complete search history.

(56) References Cited

U.S. PATENT DOCUMENTS

| | | | |
|---|---|---|---|
| 3,123,077 A | 3/1964 | Alcamo | |
| 3,981,307 A | 9/1976 | Borysko | |
| 4,744,364 A | 5/1988 | Kensey | |
| 4,805,292 A | 2/1989 | Noguchi | |
| 4,922,904 A | 5/1990 | Uetake | |
| 4,932,962 A | 6/1990 | Yoon et al. | |
| 5,041,129 A | 8/1991 | Hayhurst et al. | |
| 5,053,046 A * | 10/1991 | Janese | 606/215 |

(Continued)

FOREIGN PATENT DOCUMENTS

| | | |
|---|---|---|
| CN | 101219066 A | 7/2008 |
| CN | 2012166619 Y | 4/2009 |

(Continued)

OTHER PUBLICATIONS merriam-webster.com, stylet definition; retrieved May 4, 2015.*

(Continued)

*Primary Examiner* — Eric Rosen
*Assistant Examiner* — Mikail Mannan
(74) *Attorney, Agent, or Firm* — Knobbe Martens Olson & Bear LLP

(57) ABSTRACT

A method of improving elasticity of a tissue of a living body, the method including: forming a through-hole in the living body; inserting an insertion path forming unit, which includes a pipe member including a pipe and a support member including a support rod, into the through-hole in a state where the pipe member and the support member are assembled; removing the support member from the insertion path forming unit; coupling a medical thread supply unit to the pipe member; pushing the medical thread from behind by using a push unit; and removing the push unit, the medical thread supply unit, and the pipe member.

16 Claims, 20 Drawing Sheets

(56) References Cited

U.S. PATENT DOCUMENTS

| | | |
|---|---|---|
| 5,053,047 A | 10/1991 | Yoon |
| 5,080,667 A | 4/1992 | Chen et al. |
| 5,192,301 A | 3/1993 | Kamiya et al. |
| 5,207,694 A | 5/1993 | Broome |
| 5,224,955 A | 7/1993 | West |
| 5,236,443 A | 8/1993 | Sontag |
| 5,259,846 A | 11/1993 | Granger et al. |
| 5,269,809 A | 12/1993 | Hayhurst et al. |
| 5,306,294 A | 4/1994 | Winston et al. |
| 5,330,503 A | 7/1994 | Yoon |
| 5,500,000 A | 3/1996 | Feagin |
| 5,626,614 A | 5/1997 | Hart |
| 5,643,295 A | 7/1997 | Yoon |
| 5,683,417 A | 11/1997 | Cooper |
| 5,741,299 A | 4/1998 | Rudt |
| 5,931,855 A | 8/1999 | Buncke et al. |
| 6,241,747 B1 | 6/2001 | Ruff |
| 6,939,326 B1 | 9/2005 | Thappa |
| 7,056,331 B2 | 6/2006 | Kaplan et al. |
| 7,468,068 B2 | 12/2008 | Kolster |
| 7,582,105 B2 | 9/2009 | Kolster |
| 7,601,164 B2 | 10/2009 | Wu |
| 7,967,841 B2 | 6/2011 | Yuan et al. |
| 7,988,727 B2 | 8/2011 | Santamore et al. |
| 8,192,462 B2 | 6/2012 | Sulamanidze et al. |
| 8,747,438 B2 | 6/2014 | Longo et al. |
| 8,758,367 B2 * | 6/2014 | Philippon et al. ............ 606/139 |
| 9,044,224 B2 | 6/2015 | Lauria |
| 9,125,647 B2 | 9/2015 | Goraltchouk et al. |
| 9,204,965 B2 | 12/2015 | Longoria |
| 9,675,341 B2 | 6/2017 | D'agostino et al. |
| 2002/0198544 A1 | 12/2002 | Uflacker |
| 2003/0149447 A1 | 8/2003 | Morency et al. |
| 2004/0030319 A1 | 2/2004 | Korkor et al. |
| 2004/0153102 A1 | 8/2004 | Therin et al. |
| 2005/0101984 A1* | 5/2005 | Chanduszko ...... A61B 17/0057 606/185 |
| 2005/0240224 A1* | 10/2005 | Wu ................. A61B 17/06166 606/228 |
| 2005/0245963 A1 | 11/2005 | Kida et al. |
| 2006/0079935 A1 | 4/2006 | Kolster |
| 2006/0135994 A1 | 6/2006 | Ruff et al. |
| 2006/0135996 A1 | 6/2006 | Schwartz et al. |
| 2006/0265010 A1 | 11/2006 | Paraschac et al. |
| 2007/0038249 A1 | 2/2007 | Kolster |
| 2007/0167958 A1 | 7/2007 | Sulamanidze et al. |
| 2007/0213770 A1 | 9/2007 | Dreyfuss |
| 2008/0058816 A1 | 3/2008 | Philippon et al. |
| 2008/0132943 A1 | 6/2008 | Maiorino et al. |
| 2008/0228144 A1 | 9/2008 | Liniger et al. |
| 2008/0281357 A1 | 11/2008 | Sung et al. |
| 2009/0088797 A1 | 4/2009 | Crombie et al. |
| 2009/0093670 A1 | 4/2009 | Annest et al. |
| 2009/0112259 A1 | 4/2009 | D'Agostino |
| 2009/0210003 A1 | 8/2009 | Sulamanidze et al. |
| 2009/0299407 A1 | 12/2009 | Yuan et al. |
| 2010/0137679 A1* | 6/2010 | Lashinski et al. ............ 600/37 |
| 2010/0160961 A1 | 6/2010 | Nawrocki et al. |
| 2011/0054522 A1 | 3/2011 | Lindh et al. |
| 2011/0238111 A1 | 9/2011 | Frank |
| 2011/0270304 A1 | 11/2011 | Lee ............................. 606/222 |
| 2011/0282386 A1 | 11/2011 | Friedrich et al. |
| 2011/0288563 A1* | 11/2011 | Gianotti ............ A61B 17/0057 606/144 |
| 2012/0109193 A1* | 5/2012 | Primavera ........ A61B 17/06166 606/228 |
| 2012/0109195 A1 | 5/2012 | Odermatt et al. |
| 2012/0239002 A1 | 9/2012 | Griswold |
| 2013/0245684 A1 | 9/2013 | Ruff et al. |
| 2013/0345745 A1 | 12/2013 | Kim |
| 2014/0228971 A1 | 8/2014 | Kim |
| 2014/0364904 A1 | 12/2014 | Kim |
| 2015/0305736 A1 | 10/2015 | Kim |
| 2015/0366553 A1 | 12/2015 | Kim |
| 2016/0302905 A1 | 10/2016 | Kim |

FOREIGN PATENT DOCUMENTS

| | | | |
|---|---|---|---|
| CN | 101500495 A | 8/2009 | |
| CN | 102271734 A | 12/2011 | |
| DE | 3223153 C1 | 8/1983 | |
| DE | 102008057213 A1 | 5/2010 | |
| EP | 0314412 A1 | 5/1989 | |
| EP | 1929961 A2 | 6/2008 | |
| EP | 1955720 A1 | 8/2008 | |
| EP | 2020209 A1 | 2/2009 | |
| EP | 2108316 A2 | 10/2009 | |
| EP | 2386252 A1 | 11/2011 | |
| EP | 2386323 A2 | 11/2011 | |
| GB | 1091282 A | 11/1967 | |
| JP | 04-307050 A | 10/1992 | |
| JP | 04-307052 A | 10/1992 | |
| JP | 08-52154 A | 2/1996 | |
| JP | 08-140982 A | 6/1996 | |
| JP | 02-277459 B2 | 5/1998 | |
| JP | 10-258123 A | 9/1998 | |
| JP | 10-272182 A | 10/1998 | |
| JP | 2000-202029 A | 7/2000 | |
| JP | 3069906 U | 7/2000 | |
| JP | 2000-225118 A | 8/2000 | |
| JP | 2000-232984 A | 8/2000 | |
| JP | 2002-516585 A | 6/2002 | |
| JP | 2003-019683 A | 1/2003 | |
| JP | 2004-041492 A | 2/2004 | |
| JP | 2004-057516 A | 2/2004 | |
| JP | 2004-073403 A | 3/2004 | |
| JP | 2004-121634 A | 4/2004 | |
| JP | 2004-530524 A | 10/2004 | |
| JP | 2004-329964 A | 11/2004 | |
| JP | 2005-177499 A | 7/2005 | |
| JP | 2005-177500 A | 7/2005 | |
| JP | 2006-025867 A | 2/2006 | |
| JP | 2006-515203 A | 5/2006 | |
| JP | 2007-075616 A | 3/2007 | |
| JP | 2007-090062 A | 4/2007 | |
| JP | 2007-537017 A | 12/2007 | |
| JP | 2008-114074 A | 5/2008 | |
| JP | 2008-514382 A | 5/2008 | |
| JP | 2008-132327 A | 6/2008 | |
| JP | 2008-132328 A | 6/2008 | |
| JP | 2008-132329 A | 6/2008 | |
| JP | 2008-546454 A | 12/2008 | |
| JP | 2009-517156 A | 4/2009 | |
| JP | 2009-531071 A | 9/2009 | |
| JP | 2009-247890 A | 10/2009 | |
| JP | 2009-279393 A | 12/2009 | |
| JP | 2010-500102 A | 1/2010 | |
| JP | 2010-507453 A | 3/2010 | |
| JP | 2010-518902 | 6/2010 | ............ A61B 17/34 |
| JP | 2010-537676 A | 12/2010 | |
| JP | 2011-500208 A | 1/2011 | |
| JP | 2011-240133 A | 12/2011 | |
| JP | 2011-240134 A | 12/2011 | |
| JP | 2012-515015 | 7/2012 | ............ A61B 17/00 |
| KR | 10-0178358 B1 | 4/1998 | |
| KR | 20-0287634 Y1 | 8/2002 | |
| KR | 20-0320005 Y1 | 7/2003 | |
| KR | 10-0473108 | 12/2003 | ............ A61M 5/158 |
| KR | 10-2005-0108494 A | 11/2005 | |
| KR | 10-0761921 B1 | 10/2007 | |
| KR | 10-2008-0039345 A | 5/2008 | |
| KR | 10-2009-0035692 A | 4/2009 | |
| KR | 10-2009-0103639 A | 10/2009 | |
| KR | 10-1105647 | 8/2010 | ............ A61M 5/158 |
| KR | 10-2010-0120642 A | 11/2010 | |
| KR | 20-0451570 Y1 | 12/2010 | |
| KR | 10-2011-0019895 A | 3/2011 | |
| KR | 10-1044731 B1 | 6/2011 | |
| KR | 10-1057376 B1 | 8/2011 | |
| KR | 10-2012-0010049 A | 2/2012 | |
| KR | 10-1132841 B1 | 4/2012 | |
| KR | 10-1155817 B1 | 6/2012 | |
| KR | 10-1182337 B1 | 9/2012 | |
| KR | 10-1185583 B1 | 9/2012 | |
| KR | 10-1326763 B1 | 11/2013 | |

(56) References Cited

FOREIGN PATENT DOCUMENTS

| | | | |
|---|---|---|---|
| KR | 10-1367902 B1 | 2/2014 | |
| KR | 10-1455206 B1 | 10/2014 | |
| SU | 700121 A1 | 11/1979 | |
| SU | 1178420 A1 | 2/1984 | |
| SU | 1360705 A1 | 7/1986 | |
| WO | 2007/098212 A2 | 8/2007 | |
| WO | 2008/020937 A2 | 2/2008 | |
| WO | 2008/057261 A2 | 5/2008 | |
| WO | WO 2008/103308 | 8/2008 | ............ A61B 17/34 |
| WO | 2009/027883 A2 | 3/2009 | |
| WO | 2009/055105 A1 | 4/2009 | |
| WO | 2010/028324 A2 | 3/2010 | |
| WO | 2010/052006 A1 | 5/2010 | |
| WO | 2010/062743 * | 6/2010 | |
| WO | WO2010/062743 A1 * | 6/2010 | ........... A61B 17/064 |
| WO | 2010/080014 A2 | 7/2010 | |
| WO | 2011/128392 A1 | 10/2011 | |
| WO | 2012/144677 A1 | 10/2012 | |
| WO | 2013/169075 A1 | 6/2013 | |
| WO | 2015/083864 A1 | 6/2015 | |

OTHER PUBLICATIONS

Adib R. Karam, Curved Stylet Core Biopsy Results in Larger Cores; American Journal of Roentgenology 2010 195:1, 242-244.*

Application of related U.S. Appl. No. 15/102,240.

BD Product Catalog, Jan. 2010, BD Medical.

"Optinova ICM (TM) IV-catheter tubing", 2007, Optimus Nova.

John Jacobs Medical, "Youngs Lift", Jun. 7, 2012.

"Catheter", retrieved from http://ko.wikipedia.org/wiki/%EC%B9%B4%ED%85%8C%ED%84%B0?oldid=13222103 on or before Jan. 13, 2015.

"I.V.Catheter, Product Introduction", http://www.dukwooco.co.kr/english/product/pro_1.htm, Dukwoo Medical Co., Ltd., printed on Apr. 9, 2016.

Prado et al., "Supplemental Fixation After Endoscopic Brow Elevation Using a Single Nylon Suture", Printed from QMP's Plastic Surgery Pulse News, 2010, vol. 2, No. 1, Quality Medical Publishing, St. Louis, obtained from http://www.plasticsurgerypulsenews.com/2/article_dtl.php?QnCategoryID=18QnArticleID=45.

"Polydioxanone Suture", Metro Korea, retrieved from http://www.metrokr.com/shop/goods/goods_view.php?goodsno=186785506&category=004 on or before Oct. 30, 2015.

"Safelock Catheter", LKMEDICAL Co., Ltd. Product Catalog, retrieved from http://www.lkmedical.com on or before Oct. 30, 2015.

"Qosina, Thousands of Stock Components," 2014, Qosina Product Catalog.

"Angiocatheter", retrieved from http://medical-dictionary.thefreedictionary.com/angiocatheter on or before Oct. 2, 2015.

"Food and drug safety-wife medical equipment e-petitions", Ministry of Food and Drug Safety, retrieved from https://www.emed.mfds.go.kr/, on or before Nov. 3, 2015.

Office Communication Japanese Patent Office on third party submission of references in Japanese Patent Application 2014-549981 dated Jan. 25, 2016—20 pages.

Photos of BD Inc's Product, produced on Jul. 18, 2006, BD Inc.

"MediFirst Homepage", http://www.medifirst.co.kr, published on Nov. 5, 2013.

Japanese Office Action dated Jun. 30, 2016 of Japanese Patent Application No. 2014-207825 corresponding to related U.S. Appl. No. 14/003,390—2 pages.

* cited by examiner

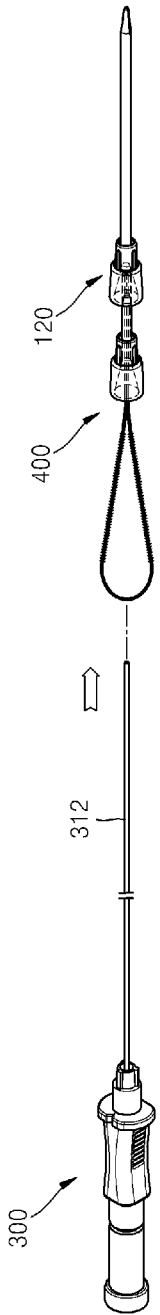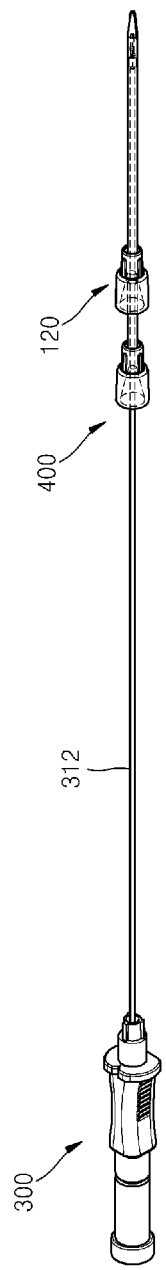

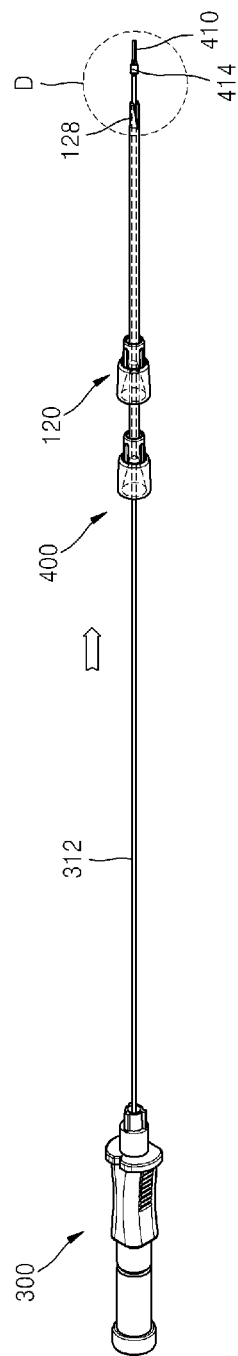
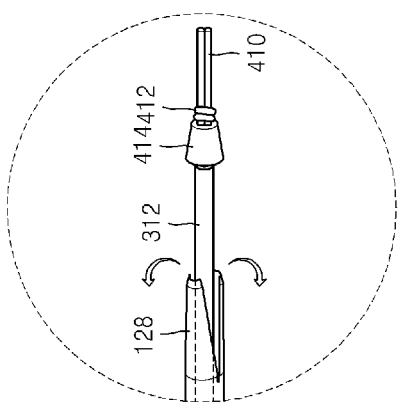
FIG. 9I
FIG. 9J

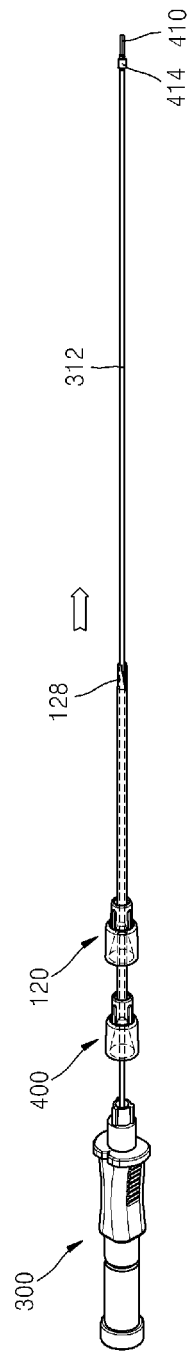
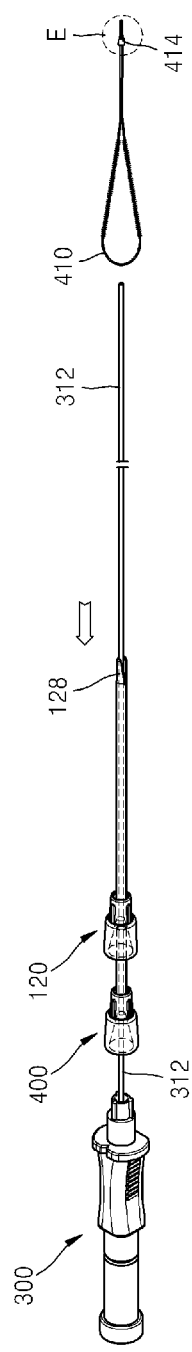

METHOD OF IMPROVING ELASTICITY OF TISSUE OF LIVING BODY

FIELD

The present disclosure relates to a surgical method for improving elasticity in a tissue. Specifically, the disclosure relates to a method of improving elasticity of a tissue by using a medical thread.

BACKGROUND

A medical thread has been used for a long time to connect or suture a damaged muscular, vascular, or nervous tissue or a surgically incised tissue. Also, a medical thread is used for a double eyelid surgery or a surgery for removing sagging or wrinkles from a skin or a tissue due to aging, reduced skin elasticity, external wound, overuse, or necrosis. A lift surgery which lifts up a loose skin or tissue and removes wrinkles on a face, jaw, neck, abdomen, vagina, breast, or hip by using a medical thread and a needle has been highlighted because it does not require excessive incision, minimizes scars, and causes slight bleeding and swelling.

However, in a conventional lift surgery using a medical thread, in order to insert and fix the medical thread into a body, one insertion through-hole is formed at a point of the body into which the medical thread is inserted and at least one fixed through-hole is formed at a point of the body to which the medical thread is fixed, the medical thread is inserted through the insertion through-hole, is pushed from behind such that a front end portion of the medical thread passes through the fixed through-hole to stick out of the fixed through-hole, and is knotted, and then a skin with the knot is sutured or a skin incision is closed.

However, since the medical thread passes through the insertion through-hole to be inserted into the skin, passes through the fixed through-hole to be discharged from the body, and then is inserted into the body to be fixed, the conventional lift surgery has problems in that a plurality of through-holes have to be formed, it is difficult to insert the medical thread into the body, it takes a lot of time to perform the conventional lift surgery, and there is a high risk because of a high level of anesthesia.

SUMMARY

The present disclosure provides a method of improving elasticity of a tissue of a living body by using a medical thread.

According to an aspect of the present disclosure, there is provided a method of improving elasticity of a tissue of a living body, the method including: forming a through-hole in the living body; inserting an insertion path forming unit, which includes a pipe member including a pipe that is hollow and forms a path through which a medical thread is to be inserted and a support member including a support rod that is inserted into the pipe of the pipe member and has a stiffness greater than a stiffness of the pipe member, into the through-hole in a state where the pipe member and the support member are assembled; removing the support member from the insertion path forming unit; coupling a medical thread supply unit to the pipe member; pushing the medical thread from behind by using a push unit that may slide in the pipe of the pipe member in a longitudinal direction of the pipe of the pipe member and pushes the medical thread through the pipe of the pipe member; and removing the push unit, the medical thread supply unit, and the pipe member.

An inclined insertion unit which is tapered may be formed on an outer surface of an end portion of the pipe member.

A two-step inclined portion which is tapered at an angle greater than an angle of the inclined insertion unit may be formed on an end portion of the inclined insertion unit.

The inclined insertion unit may further include at least one cut line that is formed in parallel to an axial direction of the pipe member to branch the end portion of the pipe member.

The pipe member may include a coupling unit including a mount groove that is hollow and tapered and receives the medical thread supply unit therein, and the medical thread supply unit includes a medical thread retaining unit including a supply pipe that is hollow and retains the medical thread to be inserted therein, wherein the medical thread retaining unit includes a connector having a complementary shape to the mount groove of the pipe member, wherein the medical thread retaining unit is coupled to the mount groove via the connector.

A medical thread support for fixing the medical thread in the tissue of the living body may be formed on an end portion of the medical thread.

The medical thread may have a loop shape and the medical thread support may be disposed at a position where both ends of the medical thread are adjoined.

The medical thread support may have a truncated cone shape whose diameter increases away from a side where the medical thread is inserted toward an opposite side.

The medical thread may include barbs that obliquely protrude toward an end portion of the medical thread at a side where the medical thread is inserted.

A maximum diameter of the medical thread support may be the same as or less than an inner diameter of the pipe of the pipe member.

A shoulder portion that protrudes inward in a radial direction may be formed on an inner surface of the mount groove.

The pipe member may include a coupling unit including a mount groove that is hollow and tapered and receives the medical thread supply unit therein, and the medical thread supply unit may include the medical thread and a medical thread support that is formed on an end portion of the medical thread and fixes the medical thread in the tissue of the living body.

The through-hole may be formed by using a through-hole forming unit that is additionally disposed on the insertion path forming unit.

The push unit may include a push rod that has a length great enough to pass through and stick out of the insertion path forming unit and the medical thread supply unit.

The method may further include, after the removing of the push unit, the medical thread supply unit, and the pipe member, adjusting an elasticity improvement direction of the tissue of the living body by pushing in a predetermined direction the tissue of the living body into which the medical thread has been inserted. The living body is living bodies of animals including human. The tissue may be a soft tissue such as a subcutaneous tissue, a muscular tissue, or a connective tissue whose elasticity needs to be improved, and may be a tissue on a face, neck, breast, arm, leg or et cetera.

DRAWINGS

The above and other features and advantages of the present invention will become more apparent by describing in detail exemplary embodiments thereof with reference to the attached drawings in which:

FIGS. 9A through 9M are perspective views for explaining a method of improving elasticity of a living body, according to an embodiment of the present disclosure;

DETAILED DESCRIPTION

Figure 1:
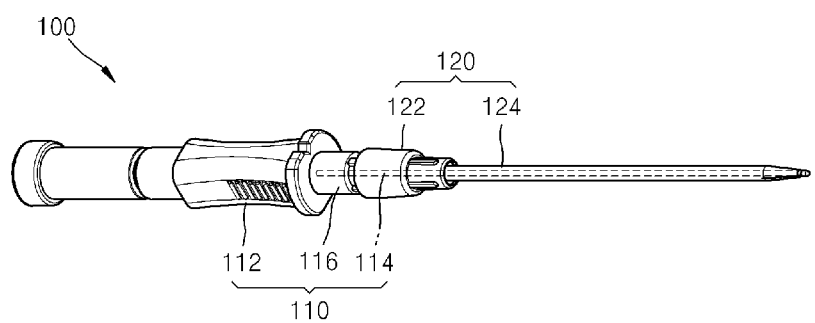
FIG. 1 is a perspective view illustrating an insertion path forming unit which is assembled, according to an embodiment of the present disclosure.

Expressions such as "at least one of," when preceding a list of elements, modify the entire list of elements and do not modify the individual elements of the list.

The present invention will now be described more fully with reference to the accompanying drawings, in which exemplary embodiments of the invention are shown. In the drawings, sizes of specific portions may be exaggerated for clarity. Accordingly, relative proportions of sizes of elements are not limited to those in the drawings of the present invention.

A method of improving elasticity of a tissue of a living body according to an embodiment of the present disclosure may be performed by using an insertion path forming unit that forms an introduction path through which a medical thread is introduced, a medical thread supply unit that supplies the medical thread, and a push unit that pushes the medical thread from behind by sliding in a longitudinal direction of the insertion path forming unit, and by further using a through-hole forming unit that forms a through-hole in the tissue of the living body into which the medical thread is to be inserted if necessary.

Figure 2:
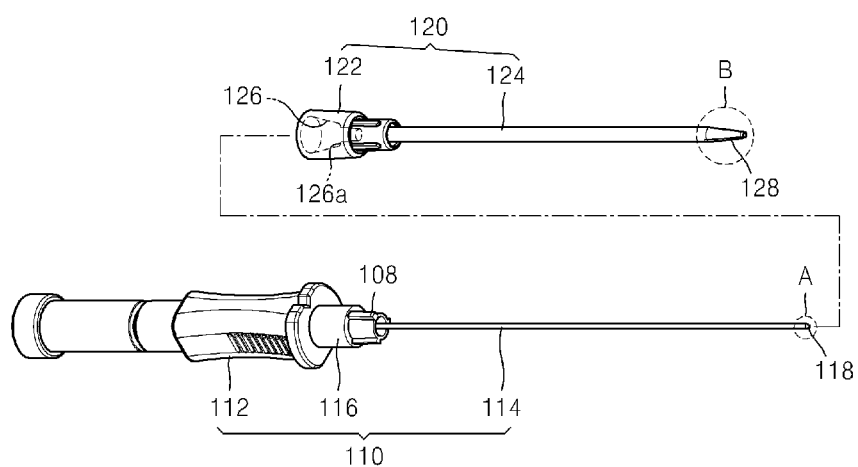
FIG. 2 is an exploded perspective view illustrating the insertion path forming unit of FIG. 1.

FIG. 1 is a perspective view illustrating an insertion path forming unit 100 which is assembled, according to an embodiment of the present disclosure. FIG. 2 is an exploded perspective view illustrating the insertion path forming unit 100 of FIG. 1.

Referring to FIGS. 1 and 2, the method of improving elasticity of the tissue of the living body uses the insertion path forming unit 100 including: a pipe member 120 including a hollow pipe 124 that forms an insertion path; and a support member 110 including a support rod 114 that is inserted into the pipe 124 of the pipe member 120 and has a stiffness greater than that of the pipe member 120.

Since the pipe member 120 of the insertion path forming unit 100 moves forward in a tissue of the living body, the pipe member 120 is formed of an elastic material having predetermined flexibility in order not to damage the tissue. For example, the pipe 124 of the pipe member 120 may be formed of a silicon material.

The pipe member 120 has flexibility and thus is not easy to move forward in the tissue of the living body. In order to solve this problem, the support member 110 of the insertion path forming unit 100 is inserted into the pipe member 120 to provide a desired level of stiffness to the pipe member 120.

The support member 110 includes the support rod 114 that elongates from a support unit 116 that extends in a longitudinal direction from a handle 112 of the support member 110 which an operator (or a surgeon) holds. A front end portion 118 is formed on the support rod 114 opposite to the handle 112.

In FIGS. 1 and 2, the insertion path forming unit 100 moves rightward in the tissue of the living body.

The support rod 114 of the support member 110 may be slidably inserted into the pipe 124 of the pipe member 120, and may be separated from the pipe 124 of the pipe member 120 when the operator pulls the handle 112 backward (leftward in FIGS. 1 and 2).

The pipe member 120 includes a coupling unit 122 including a mount groove 126 into which an insertion unit 108 protruding with a diameter less than that of the support unit 116 formed on the handle 112 of the support member 110 is inserted. An inner surface of the mount groove 126 is inclined as the mount groove 126 is tapered to change its diameter.

A shoulder portion 126a protruding inward in a radial direction is formed on the inner surface of the mount groove 126 to receive any to-be-coupled member.

Accordingly, the front end portion 118 of the support member 110 passes through the mount groove 126 of the pipe member 120 and is disposed inside the pipe 124 not to pass through an inclined insertion unit 128 of the pipe member 120. In a state where the support member 120 is completely inserted into the pipe member 120, the front end portion 118 of the support member 110 extends substantially to the inclined insertion unit 128 of the pipe member 120 and supports the inclined insertion unit 128.

Figure 3A:
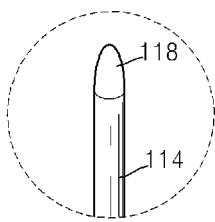
FIGS. 3A and 3B are enlarged views illustrating a portion A of FIG. 2, according to various embodiments of the present disclosure.
Figure 3B:
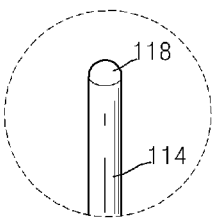

FIGS. 3A and 3B are enlarged views illustrating a portion A of FIG. 2, according to embodiments of the present disclosure.

Referring to FIG. 3A, the front end portion 118 of the support rod 114 of the support member 110 may be formed to have a partially oval cross-sectional shape. Referring to FIG. 3B, the front end portion 118 of the support rod 114 of the support member 110 may be formed to have a partially circular cross-sectional shape. Since the support rod 114 is inserted into the pipe 124 of the pipe member 120, an outer diameter of the support rod 114 may be the same as or less than an inner diameter of the pipe 124 of the pipe member 120.

FIGS. 4A through 4E are enlarged views illustrating the inclined insertion unit 128 when the pipe member 120 passes through the tissue of the living body, according to embodiments of the present disclosure.

Referring to FIGS. 4A through 4E, the inclined insertion unit 128 is formed on an end portion of the pipe 124 of the pipe member 120 to be tapered, and a two-step inclined portion 129 that is tapered at an angle greater than that of the inclined insertion unit 128 is formed on an end portion of the inclined insertion unit 128.

An outlet 127 which is hollow is formed at the center of the two-step inclined portion 129. A medical thread assembly including a medical thread and a support is discharged through the outlet 127. An inner diameter D1 of the outlet 127 has a size great enough for the medical thread assembly to pass through the outlet 127. The medical thread assembly is formed to have a size less than that of the inner diameter D1, and may pass through the outlet 127 while elastically expanding the outlet 127, instead of loosely passing through the outlet 127.

Figure 4A:
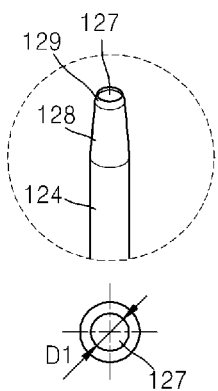
FIGS. 4A through 4E are enlarged views illustrating a portion B of FIG. 2, according to various embodiments of the present disclosure.
Figure 4B:
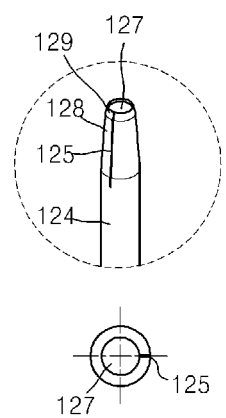

In FIG. 4A, in order for the medical thread assembly to pass through the outlet 127 while elastically expanding the outlet 127, no cut line is formed on the inclined insertion unit 128. However, in FIG. 4B, one cut line 125 is formed on the inclined insertion unit 128 in parallel to the longitudinal direction. Accordingly, when the medical thread assembly passes through and is discharged from the outlet 127, the inclined insertion unit 128 is curved along the cut line 125, thereby enabling the medical thread assembly to easily pass through and be discharged from the outlet 127.

Figure 4C:
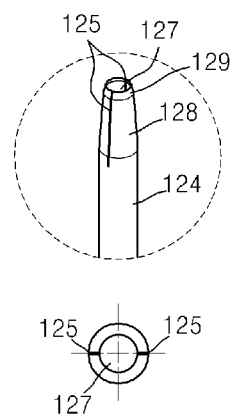
Figure 4D:
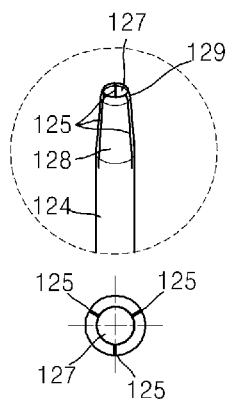
Figure 4E:
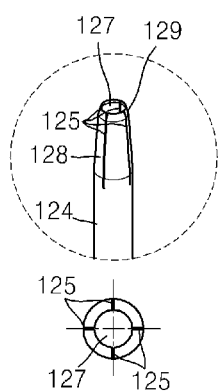

In FIG. 4C, two cut lines 125 are formed to face each other about the outlet 127. In FIG. 4D, three cut lines 125 are formed at intervals of 120° about the outlet 127. In FIG. 4E, four cut lines 125 are formed at intervals of 90° about the outlet 127.

Figure 5:
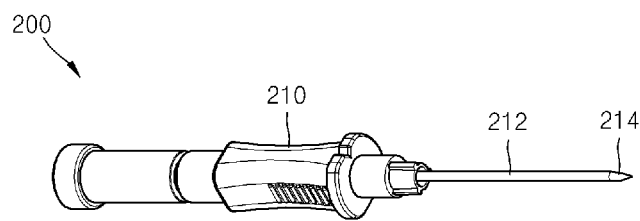
FIG. 5 is a perspective view illustrating a through-hole forming unit additionally disposed on the insertion path forming unit, according to an embodiment of the present disclosure.
Figure 6:
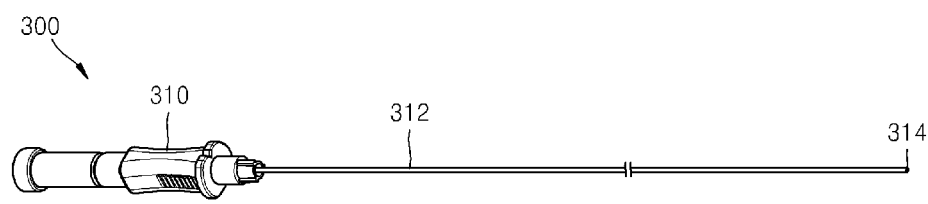
FIG. 6 is a perspective view illustrating a push unit according to an embodiment of the present disclosure.

FIG. 5 is a perspective view illustrating a through-hole forming unit 200 additionally disposed on the insertion path forming unit 100 to form a through-hole in the living body, according to an embodiment of the present disclosure. The through-hole forming unit 200 is provided in order to mark a start position of the insertion path forming unit 100 and to secure a substantial movement path through which the insertion path forming unit 100 moves in the tissue.

The through-hole forming unit 200 includes a through-hole unit 214 that is formed on an end portion of a long through-hole rod 212 in order to form a through-hole in the tissue, and a handle 210 that is formed on an end portion of the through-hole rod 212 opposite to the through-hole unit 214.

An operation of pushing the medical thread from behind in the method of the present disclosure is performed by using a push unit 300 for pushing the medical thread in a medical thread supply unit 400 (see FIG. 7A) coupled to the pipe member 120 after the support member 110 is removed from the insertion path forming unit 100 of FIG. 1.

The push unit 300 includes a handle 310 which the operator holds, a push rod 312 that extends from the handle 310, and a push unit 314 that is formed on an end portion of the push rod 312 and pushes the medical thread by contacting the medical thread.

The push rod 312 is formed to have a length great enough to pass through and stick out of the insertion path forming unit 100 and the medical thread supply unit 400.

Figure 7A:
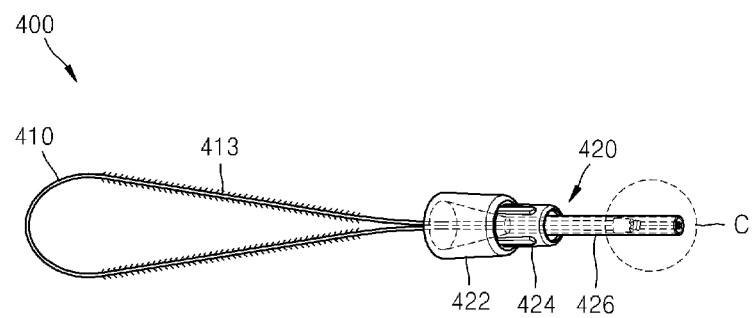
FIG. 7A is a perspective view illustrating a medical thread supply unit according to an embodiment of the present disclosure.
Figure 7B:
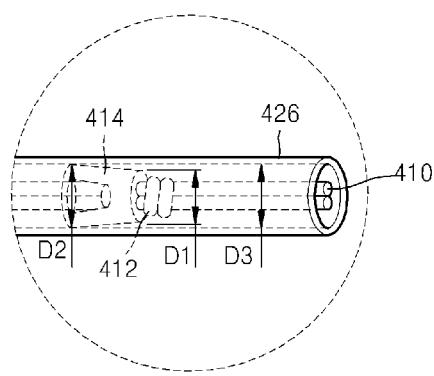
FIG. 7B is a partial enlarged view illustrating a portion C of FIG. 7A.

FIG. 7A is a perspective view illustrating the medical thread supply unit 400 that supplies the medical thread, according to an embodiment of the present disclosure. FIG. 7B is an enlarged view illustrating a portion C of FIG. 7A.

Referring to FIGS. 7A and 7B, the medical thread supply unit 400 is connected to the pipe member 120 after the support member 110 is removed in a state where the insertion path forming unit 100 is inserted into the tissue of the living body, a path through which the medical thread is inserted is secured, and the pipe member 120 is kept inserted into the tissue of the living body.

The pipe member 120 includes the coupling unit 122 including the mount groove 126 (see FIG. 2) to which the medical thread supply unit 400 is connected. The medical thread supply unit 400 includes a medical thread retaining unit 420 in which a medical thread 410 to be inserted is retained inside a supply pipe 426.

In this case, the medical thread retaining unit 420 includes a main body 422 on which a connector 424 having a complementary shape to the mount groove 126 of the pipe member 120 and coupled to the mount groove 126 is formed.

Referring to FIG. 7B, a medical thread support 414 for fixing the medical thread 410 in the tissue of the living body is formed on an end portion of the medical thread 410, and is disposed inside the supply pipe 426.

In the medical thread supply unit 400 of FIGS. 7A and 7B, the medical thread 410 has a loop shape and the medical thread support 414 is disposed at a position where both ends of the medical thread 410 are adjoined. In this case, the medical thread support 414 may have a truncated cone shape whose diameter increases away from a side where the medical thread 410 is inserted (right side in FIGS. 7A and 7B) toward an opposite side (left side in FIGS. 7A and 7B). That is, as shown in FIG. 7B, a diameter D1 of an end portion of the medical thread support 414 at a side where the medical thread 410 is inserted is less than a diameter D2 of an opposite end portion of the medical thread support 414, and an inner diameter D3 of the supply pipe 426 may be the same as or greater than the diameter D2 of the medical thread support 414.

In order to define a position of the medical thread support 414 in the supply pipe 426, a knot 412 is formed on an end portion of the medical thread 410 in a longitudinal direction of the medical thread 410.

Figure 8:
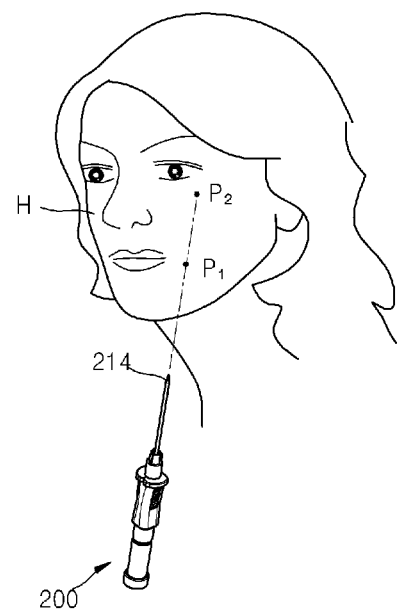
FIG. 8 is a perspective view for explaining an operation of forming a through-hole in a skin by using the through-hole forming unit, according to an embodiment of the present disclosure.

FIG. 8 is a perspective view illustrating a position P1 at which a medical thread is inserted into a face and a position P2 at which the medical thread is fixed, according to an embodiment of the present disclosure. That is, a through-hole is formed by inserting the through-hole forming unit 200 at the position P1 where the medical thread is introduced into a tissue, and the medical thread is inserted into the tissue by the insertion path forming unit 100 inserted at the position P1, and is fixed to the tissue by the medical thread support 414 at the position P2.

FIGS. 9A through 9M are perspective views for explaining an order in which elements are used in the method for improving the elasticity of the tissue of the living body, according to an embodiment of the present disclosure.

Figure 9A:
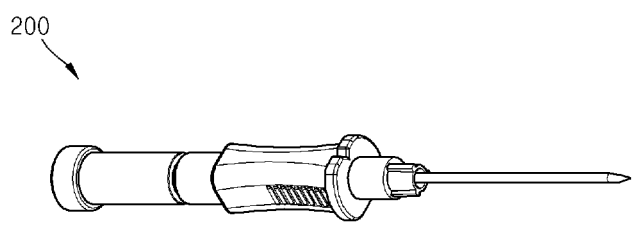
Figure 9B:
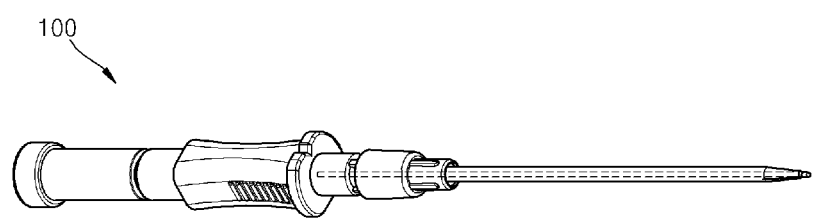

Referring to FIGS. 8 and 9A, a through-hole is formed at the position P1 of the living body by using the through-hole forming unit 200. Next, the operator introduces the insertion path forming unit 100 at the position P1 from which the through-hole forming unit 200 is taken out as shown in FIG. 9B. In a state where the support member 110 is coupled to the pipe member 120, the insertion path forming unit 100 is inserted into the tissue of the living body. In this case, since the pipe member 120 is flexible, it is not easy for the pipe member 120 to be introduced into the tissue. However, since the support member 110 having a stiffness greater than that of the pipe member 120 is inserted into the pipe member 120 and acts as a frame of the pipe member 120, the insertion path forming unit 100 may be easily introduced substantially to the position P2 in the tissue.

Figure 9C:
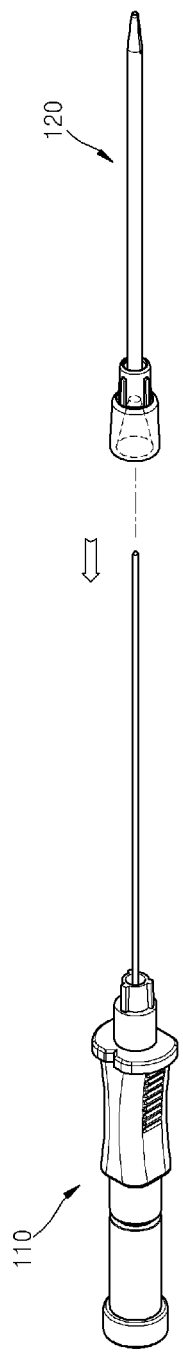

Referring to FIG. 9C, once an end portion of the insertion path forming unit 100 is introduced substantially to the position P2 of the tissue, the operator separates only the support member 110 backward from the insertion path forming unit 100 in a state where the pipe member 120 is inserted into the tissue.

Figure 9D:
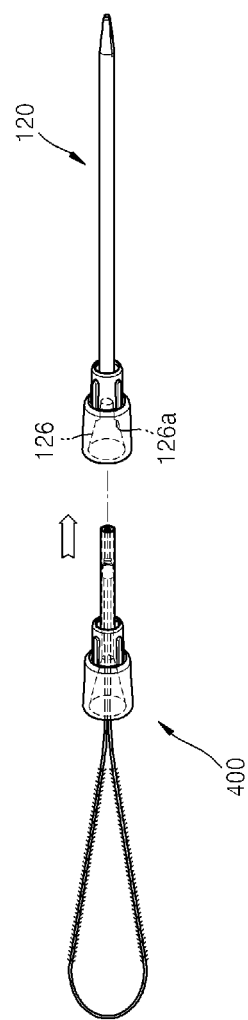
Figure 9E:
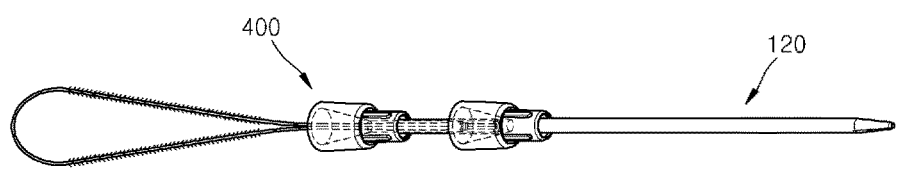

Referring to FIGS. 9D and 9E, the medical thread supply unit 400 is inserted into the pipe member 120 from which the support member 110 has been separated. In this case, since the shoulder portion 126a protruding inward in the radial direction is formed on the inner surface of the mount groove 126, when an end portion of the medical thread supply unit 400 is received in the mount groove 136 of the pipe member 120, an end portion of the supply pipe 426 (see FIG. 7A) is mounted on the shoulder portion 126a.

Figure 9F:
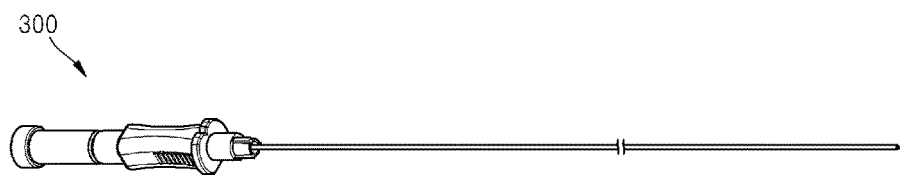

In a state where the medical thread supply unit 400 is coupled to the pipe member 120 of the insertion path forming unit 100, the push unit 300 is prepared as shown in FIG. 9F and the operator pushes the medical thread 410 of the medical thread supply unit 400 connected to the pipe member 120 from behind by using the push unit 300 as shown in FIGS. 9G and 9H.

Once the operator pushes the medical thread 410 of the medical thread supply unit 400 by using the push unit 300, the medical thread 410 passes through the supply pipe 426 of the medical thread supply unit 400, is guided into the pipe member 120 of the insertion path forming unit 100, and is discharged through the outlet 127 of the inclined insertion unit 128 formed on the end portion of the pipe member 120.

When the medical thread 410 is discharged through the inclined insertion unit 128 of the pipe member 120, the inclined insertion unit 128 may be curved such that a diameter of the inclined insertion unit 128 is increased to easily discharge the medical thread 410. For example, as shown in FIG. 9J, the diameter of the inclined insertion unit 128 is increased along cut lines formed on the inclined insertion unit 128, and the medical thread 410 and the medical thread support 414 are discharged through the outlet 127 of the inclined insertion unit 128 whose diameter has been increased.

Referring to FIG. 9K, the operator additionally pushes the push unit 300 and accurately locates the medical thread support 414 of the medical thread 410 at a fixed position in the tissue. Since the medical thread support 414 has a truncated cone shape and may move only in one direction toward a smaller diameter, a position of the medical thread support 414 is determined by additionally pushing the push unit 300.

Once the medical thread support 414 reaches and is fixed to a predetermined position, as shown in FIG. 9I, the push unit 400, the medical thread supply unit 400, and the pipe member 120 of the insertion path forming unit are moved backward to be taken out. Accordingly, the medical thread 410 is completely discharged from the inclined insertion unit 128 and is disposed in the tissue.

Figure 9M:
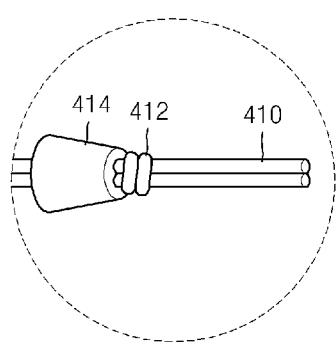

Referring to FIG. 9M, the medical thread support 414 of the medical thread 410 is fixed to a predetermined point of the tissue due to its truncated cone shape, and barbs 413 formed on the medical thread 410 catch hold of the tissue. To this end, the medical thread 410 includes the barbs 413 that obliquely protrude toward an end portion of the medical thread 410 at a side where the medical thread 410 is inserted (right side in FIG. 9M).

Next, the operator adjusts a direction in which elasticity of the tissue of the living body is to be improved by pushing the tissue of the living body in a predetermined direction when the medical thread 410 is fixedly inserted.

The medical thread support 414 of the medical thread 410 may be formed of a non-absorbable material which is not absorbed into the living body, or an absorbable material as desired. For example, the medical thread support 414 of the medical thread 410 may be formed of, but is not limited to, nylon, polypropylene (e.g., polypropylene mesh), polyvinylidene fluoride, polyester, stainless steel, gold, titanium, silicon, medpore, gore-tex, mesh, polyactic acid, polydioxanone (PDO, PDS), or a copolymer of lactic acid and glycolic acid. When the medical thread support 414 of the medical thread 410 is formed of an absorbable material that may be absorbed into the living body, the medical thread support 414 does not have to be removed after suture is performed in the living body.

A length of the medical thread support 414 of the medical thread 410 may range, for example, from about 1 mm to about 10 mm, but the present embodiment is not limited thereto and the length of the medical thread support 414 may be adjusted according to where and why to use the medical thread support 414. A diameter of a front end of the medical thread support 414 whose diameter is relatively small may range from about 0.1 mm to about 2 mm and a diameter of a rear end of the medical thread support 414 whose diameter is relatively large may range from about 0.5 mm to about 5 mm, but the present embodiment is not limited thereto and the diameters may be adjusted according to a thickness and use of the medical thread 410.

One, two, three, or four or more medical threads 410 with the barbs 413 may be used, and the number of the medical threads 410 may be appropriately adjusted according to a thickness and use of the medical threads 410, and each of the medical threads 410 may be obtained by twisting or braiding a single strand or multiple strands.

The barbs 413 may be arranged on the medical thread 410 according to a desired configuration, and may be formed by using any of appropriate methods including well-known methods in the field. Examples of the well-known methods may include injection molding using pressure, stamping, and cutting by knife or laser. A desired number of acute angular cuts are made by using the medical thread 410. A size of each of the barbs 413 may be appropriately adjusted according to a use within the scope of the present disclosure. For example, a depth of each of the barbs 413 formed on the medical thread 410 may range from about 30 microns ($\mu$) to about 100$\mu$, and may be adjusted according to a diameter of the medical thread 410. A distance between the barbs 413 formed on the medical thread 410 may range from about 100$\mu$ to about 1 mm, or more.

The medical thread 410 may be formed of any of various materials, for example, a polymer material, a metal material, and a biological material. For example, the medical thread 410 may be formed of, but is not limited to, a non-absorbable material such as polypropylene, gold, stainless steel, titanium, nylon, polyvinylidene fluoride, polyester, or braided silk, or an absorbable material such as polydioxanone (PDO, PDS).

Figure 10A:
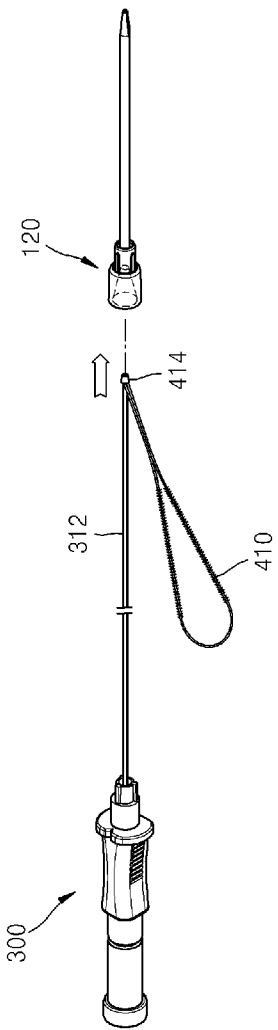
FIGS. 10A and 10B are perspective views for explaining an order in which elements are used in the method for improving the elasticity of the living body, according to an embodiment of the present disclosure.
Figure 10B:
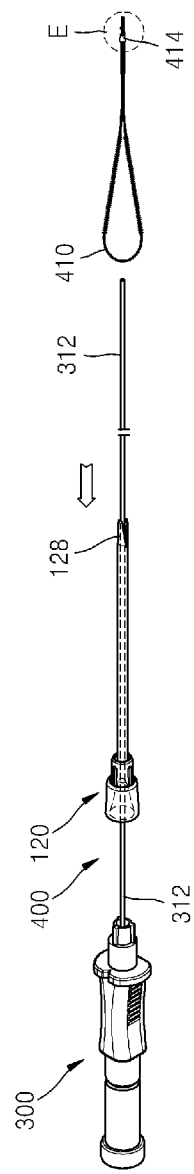

FIGS. 10*a* and 10B are perspective views for explaining an operation of inserting the medical thread 410, according to an embodiment of the present disclosure. FIGS. 10A and 10B are a modified example of FIGS. 9G and 9I.

Referring to FIGS. 10A and 10B, a structure of the medical thread supply unit 400 of FIGS. 9G and 9I is modified. The medical thread supply unit 400 of FIGS. 10*a* and 10B includes the medical thread 410 and the medical thread support 414 that is formed on an end portion of the medical thread 410 and fixes the medical thread 410 in the tissue of the living body. That is, the medical thread supply unit 400 of FIGS. 10A and 10B is obtained by omitting the medical thread retaining unit 420 from the medical thread supply unit 400 of FIG. 7A.

Accordingly, referring to FIGS. 10A and 10B, the medical thread supply unit 400 including the medical thread 410 and the medical thread support 414 that is formed on the end portion of the medical thread 410 is inserted into an end portion of the push rod 312 of the push unit 300, is fixed to be separable from the push rod 312, and is inserted into the pipe member 120 to push the medical thread 410.

The method of improving the elasticity of the tissue of the living body according to the present disclosure may be applied to a tissue whose elasticity needs to be improved such as a subcutaneous tissue, a muscular tissue, or a connective tissue. Also, the method may be applied to a tissue on a mid-face, a forehead, a cheek, a jaw, a neck, a breast, or a joint. FIGS. 15A through 15E are views illustrating a position P1 at which the medical thread 410 is inserted and a position P2 at which the medical thread 410 is fixed on a forehead (see FIG. 15A), a neck (see FIG. 15B), a cheek (see FIG. 15C), a jaw (see FIG. 15D), and a breast (see FIG. 15E), and illustrating the barbs 413 that obliquely protrude toward an end portion of the medical thread at a side where the medical thread is inserted.

The method of improving the elasticity of the tissue of the living body of the present disclosure will be described in further detail. However, the present embodiment is not limited to the following description.

Operation 1: Design

Figure 11:
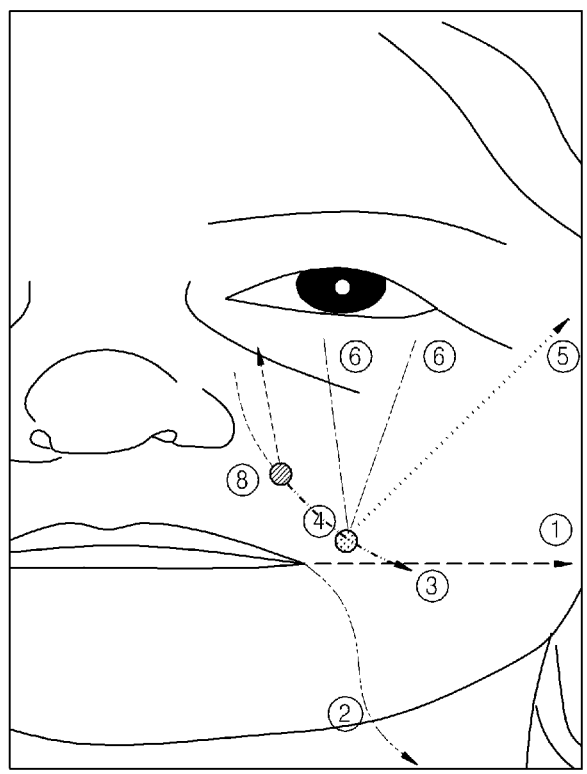
FIG. 11 is a view for explaining a selective operation of designing a position where a through-hole is to be formed and a position where elasticity is to be improved, according to an embodiment of the present disclosure.

A position where a through-hole is to be formed in a face and a position where elasticity of the tissue is to be improved are designed as follows (see FIG. 11).

(1) Mark a point that is horizontally connected to a mouth corner.
(2) Mark a marionette's line.
(3) Mark a nasolabial groove line.
(4) Mark the through-hole position on the nasolabial groove line.
(5) Mark a direction in which elasticity is to be improved by pushing up with a hand.
(6) Recheck the direction in which elasticity is to be improved and mark another direction in which elasticity is to be improved.
(7) Perform steps (1) through (6) on an opposite side of the face.
(8) When a tear through under the eye is to be corrected, mark another hole in the face.

Operation 2: Anesthesia

Anesthesia is performed by using a mixture of 5 cc of saline and 5 cc of 2% lidocaine with 1:80,000 to 1:100,000 epinephrine as an anesthetic solution, a maximum dosage for infiltration local anesthesia is 7 mg/kg for lidocaine with epinephrine and is 4.5 mg/kg for lidocaine without epinephrine, not to exceed 300 mg.

Figure 12:
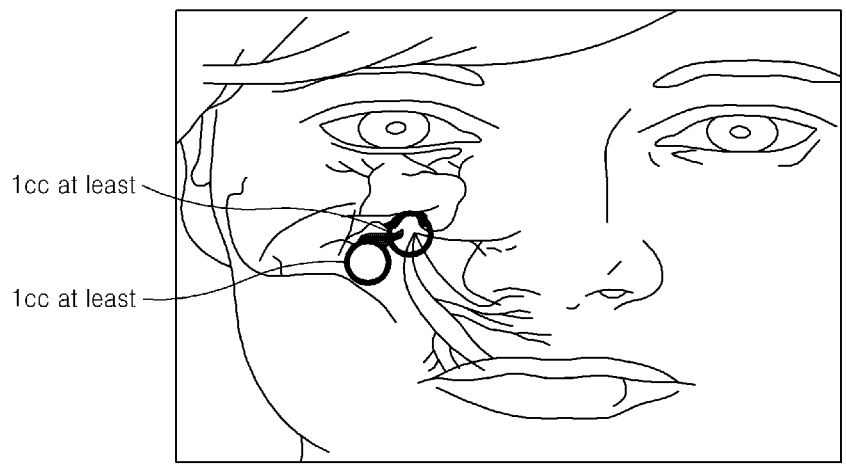
FIG. 12 is a view for explaining a selective operation of performing anesthesia, according to an embodiment of the present disclosure.

The anesthetic solution is injected into a central portion of the face at the through-hole position marked on the nasolabial groove line. First, 1 cc or more of diluted local anesthetic solution is injected around a bone at an infraorbital nerve, a syringe is exchanged and a needle is moved slightly backward to change a direction, and 1 cc or more of local anesthetic solution is injected around a periosteum in the middle (see FIG. 12).

Operation 3: Surgery

Figure 13:
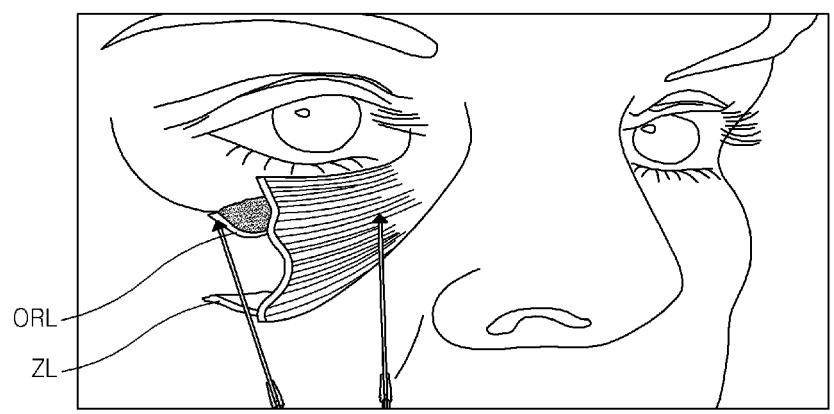
FIG. 13 is a view for explaining a position at which the insertion path forming unit may be inserted in the method of improving the elasticity of the tissue of the living body, wherein ORL denotes an orbital rim ligament and ZL denotes a zygomatic ligament, according to an embodiment of the present disclosure.

As shown in FIG. 13, a surgery is performed from an outer portion of the face to an inner portion of the face. In principle, one through-hole is formed. However, when a distance between a positions where the medical thread 410 is inserted and a position where the medical thread 410 is inserted again is too large or directions in which the tissue is to be lifted are excessively different, two or more through-holes may be performed.

Figure 14:
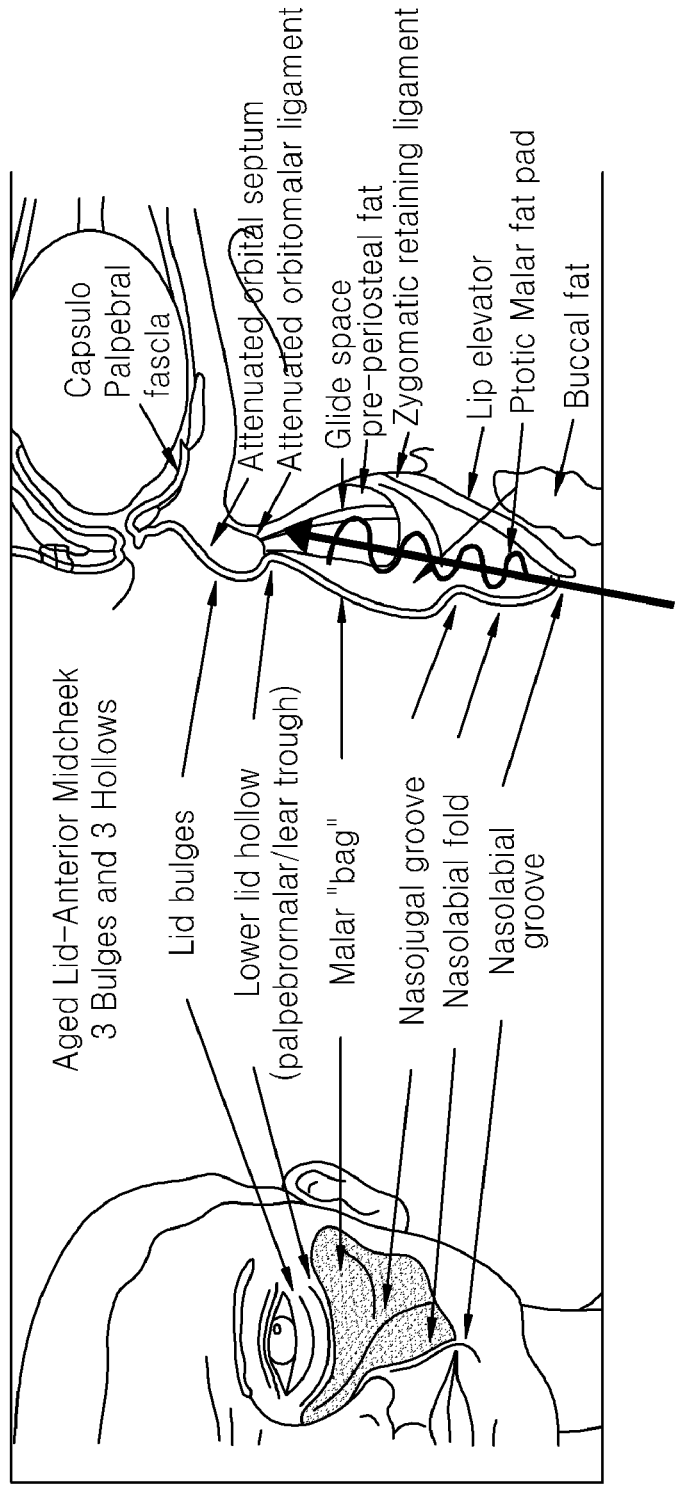
FIG. 14 is a view illustrating anatomical positions through which the insertion path forming unit passes.
Figure 15A:
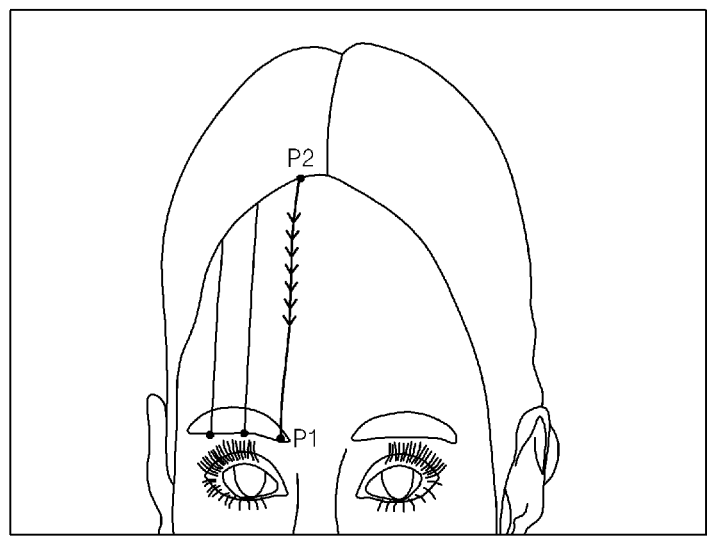
FIGS. 15A through 15E are views for explaining a position at which the medical thread is inserted, a position at which the medical thread is fixed, and a direction in which barbs protrude in each portion of the living body.
Figure 15B:
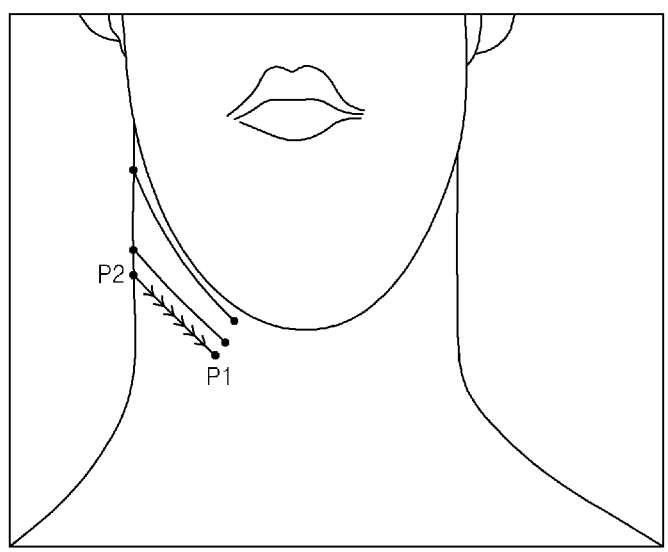
Figure 15C:
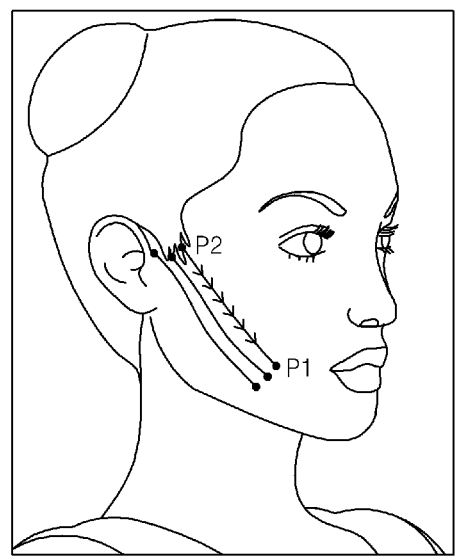
Figure 15D:
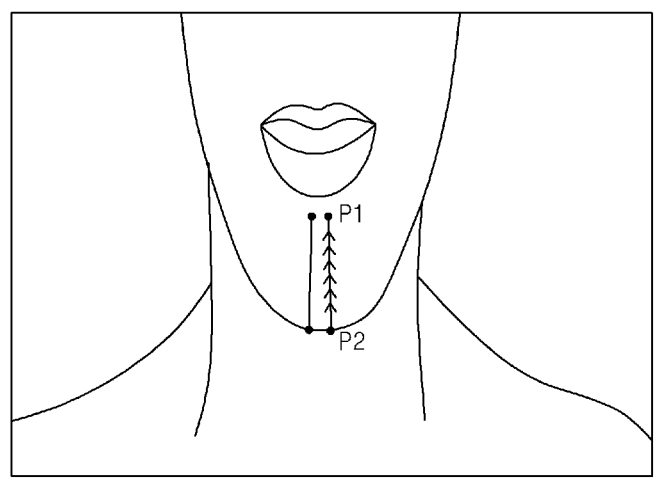
Figure 15E:
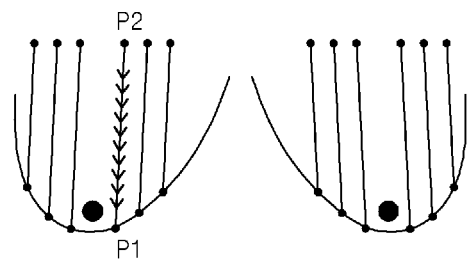

The insertion path forming unit 100 including the pipe member 120 and the support member 110 which are assembled is inserted into a through-hole, the tissue is held with a hand, and the insertion path forming unit 100 is inserted from a subcutaneous fat layer to a periosteum under the eye while being rotated. When there is a resistance of the tissue, the insertion path forming unit 100 is inserted while being rotated without being forcibly inserted. When the insertion path forming unit 100 reaches an area under the eye, the operator softly presses a bone under the eye to protect the eyeball. FIG. 14 is a view illustrating anatomical positions through which the insertion path forming unit 100 passes. When the insertion path forming unit 100 reaches a desired position, only the support member 110 is removed. Next, the medical thread supply unit 400 is coupled to the pipe member 120, the medical thread 410 having a loop shape is cut, and the medical thread 410 is gently pushed from behind by the push unit 300. When the medical thread 410 reaches the desired position, the operator softly presses the bone under the eye, and removes the push unit 300, the medical thread supply unit 400, and the pipe member 120. In a state where the medical thread 410 having two ends is tightened, the tissue is pushed several times in a predetermined direction to adjust an elasticity improvement direction. In this case, the medical thread 410 should not be strongly pulled because the medical thread support 414 may be separated. When the medical thread 410 is cut by using scissors, the medical thread 410 is cut one end after the other end while the tissue is deeply pressed. In order to prevent a dimple in the tissue, an area around the through-hole is pinched. The same steps are performed in another lifting direction and on an opposite side of the face. When the through-hole is large, the through-hole is tied with nylon 6-0 or 7-0, and the nylon is removed 2 or 3 days after the surgery.

As described above, a method of improving elasticity of a tissue of a living body of the present disclosure has the following advantages.

First, since a support fixed to the tissue of the living body is formed on a medical thread that is inserted, and thus only a through-hole for inserting an end portion of the medical thread into the tissue of the living body needs to be formed in the tissue of the living body, damage to the tissue of the living body may be reduced.

Second, since a surgery for preventing wrinkles of a skin may end only by inserting the medical thread into one through-hole, the surgery may be simplified.

Third, since an end portion of an insertion path forming unit for inserting the medical thread into a through-hole is tapered such that the medical thread may pass through the insertion path forming unit and the end portion of the insertion path forming unit may be easily introduced into the tissue of the living body, frication during introduction into the tissue of the living body may be reduced.

Fourth, a pipe member of the insertion path forming unit into which the medical thread is inserted is flexible and thus may not easily move in the tissue of the living body. However, since the insertion path forming unit moves forward in the tissue of the living body in a state where a support member having a stiffness greater than that of the pipe member is inserted into the pipe member, an insertion path may be easily formed.

Fifth, since a frictional force applied when the insertion path forming unit is introduced may be further reduced by forming a tapered two-step inclined portion that is tapered at an angle greater than that of an inclined insertion unit on the inclined insertion unit that is formed on an end portion of the insertion path forming unit, a surgery may be facilitated.

Sixth, since a cut line is formed on an end portion of the inclined insertion unit, the medical thread on which the support for supporting the medical thread at a predetermined point in the tissue is formed may be easily separated from the inclined insertion unit.

Seventh, since an additional push unit is provided such that the medical thread whose stiffness is not sufficient may be introduced into the tissue of the living body, the medical thread may be introduced into the tissue of the living body without difficulty with the help of the push unit.

Eighth, since a medical thread supply unit may be inserted into the pipe member after an insertion path of the medical thread is formed and thus the medical thread does not interfere when the insertion path is formed, the insertion path may be easily formed and damage to the medical thread may be avoided.

Ninth, since an operation of inserting the medical thread is facilitated, a total time taken to perform the operation of inserting the medical thread may be reduced.

Tenth, the medical thread may be inserted into a predetermined position of the tissue of the living body and may be firmly fixed to the predetermined position.

Eleventh, since the medical thread which may lift up the tissue is inserted into the living body, a loose skin or tissue may be lifted and wrinkles may be removed.

While the present disclosure has been particularly shown and described with reference to exemplary embodiments thereof, it will be understood by those of ordinary skill in the art that various changes in form and details may be made therein without departing from the spirit and scope of the present invention as defined by the following claims.

In particular, although a method of improving elasticity of a tissue of a living body of the present disclosure has been described by referring to a lift surgery (so called, facelift) for reducing wrinkles of a face skin, the present disclosure is not limited thereto. The method may be used for aesthetic enhancement to lift a loose skin or tissue and reduce wrinkles on any of various portions of bodies including human and non-human animal bodies, and may also be used for medical treatment to improve elasticity of a tissue of a living body. Accordingly, the technical scope of the present invention has to be defined by the appended claims.

What is claimed is:

1. A method of performing a facial tissue lifting surgery, the method comprising:
    forming a through-hole into a first location of facial skin of a subject's face;
    inserting an insertion path forming unit, into the through-hole, to form an insertion path underneath the facial skin from the through-hole to a target area located underneath a second location of the facial skin of the subject's face, the insertion path forming unit comprising a hollow pipe and a support rod inserted into the hollow pipe, wherein upon forming the insertion path, a distal end of the hollow pipe reaches the target area located underneath the second location of the facial skin while a proximal end of the hollow pipe stays outside the facial skin;
    removing the support rod from the hollow pipe while maintaining the hollow pipe underneath the facial skin;
    providing a thread device and a thread supply device comprising a supply pipe, the thread device comprising a thread support, a thread attached to the thread support and barbs projecting from the thread, wherein the thread device is loaded with the thread supply device such that the entire thread support is located inside the supply pipe of the thread supply device and at least part of the thread is located outside the supply pipe;
    subsequently, engaging the thread supply device with the insertion path forming unit such that a distal end of the supply pipe of the thread supply device is coupled with the proximal end of the hollow pipe;
    subsequently, while maintaining the hollow pipe underneath the facial skin, pushing the thread device loaded with the thread supply device using a pushing rod such that the thread device travels into the hollow pipe from the supply pipe and further travels through the hollow pipe in a direction toward the target area, such that the thread support reaches the target area out of the distal end of the hollow pipe located underneath the second location of the facial skin, and such that the thread generally extends along the direction underneath the facial skin between the target area and the through-hole;
    subsequently, removing the hollow pipe from the insertion path while keeping the thread support within the target area such that, after removing the hollow pipe, the thread extends underneath the facial skin between the target area and the through-hole and further extends outside the through-hole and such that the barbs projecting from the thread are inclined toward the target area and further such that acute angles are formed between of the barbs and the direction toward the target area; and
    subsequently, fixing the thread support at the target area underneath the second location of the facial skin of the subject with the thread extending underneath the facial skin between the target area and the through-hole, in which the acute angles are formed between the barbs and the direction toward the target area.

2. The method of claim 1, wherein the hollow pipe comprises a tapered distal end portion, wherein the acute angles are formed throughout the extension of the thread underneath the facial skin between the target area and the through-hole.

3. The method of claim 2, wherein the tapered distal end portion comprises at least two different slopes with respect to a longitudinal axis of the hollow pipe.

4. The method of claim 2, wherein the tapered distal end portion comprises at least one cut line extending in a longitudinal direction of the hollow pipe.

5. The method of claim 1, wherein the thread device comprises a single strand of the thread, wherein the thread support is attached to an end portion of the thread.

6. The method of claim 1, wherein the thread of the thread device forms a closed loop and the thread support is attached to a portion of the loop.

7. The method of claim 1, wherein the thread support has a truncated cone shape.

8. The method of claim 1, wherein only one through-hole is formed during the tissue lifting surgery for the thread device.

9. The method of claim 1, wherein the insertion path is formed underneath and along the facial skin such that the target area is located higher than the first location in the subject's body.

10. The method of claim 1, wherein the first location is on or adjacent a mouth corner, a marionette's line, and a nasolabial groove line of the subject, wherein the insertion path formed underneath and along the facial skin is generally toward an eye of the subject.

11. The method of claim 1, wherein the first location is on a cheek of the subject, wherein the insertion path formed underneath and along the facial skin is directed toward an ear of the subject.

12. The method of claim 1, wherein the first location is on an eyebrow of the subject, wherein the insertion path formed underneath and along the facial skin is directed away from an eye below the eyebrow of the subject.

13. The method of claim 1, wherein the target area is located lower than the first location in the subject's body.

14. The method of claim 1, further comprising:
pulling the thread from outside the through-hole in a direction away from the second location; and
cutting a portion of the thread extending outside the through-hole while pressing a portion of the facial skin over the thread.

15. The method of claim 1, further comprising:
pulling the thread from outside the through-hole in a direction away from the second location.

16. The method of claim 1, wherein the thread support comprises a wider end and a narrower end that is narrower than the wider end, wherein the thread comprises a knot on the side of the narrower end and further comprises at least one strand extending from the wider end.

* * * * *

UNITED STATES PATENT AND TRADEMARK OFFICE
CERTIFICATE OF CORRECTION

PATENT NO. : 10,010,317 B2
APPLICATION NO. : 13/706108
DATED : July 3, 2018
INVENTOR(S) : Young Jae Kim Page 1 of 1

It is certified that error appears in the above-identified patent and that said Letters Patent is hereby corrected as shown below:

In the Specification

In Column 8 at Line 25, change "*polyactic*" to --*polylactic*--.

In Column 9 at Line 7, change "*10a*" to --*10A*--.

In Column 9 at Line 13, change "*10a*" to --*10A*--.

In the Claims

In Column 12 at Line 52, after "between" delete "of".

Signed and Sealed this
Twenty-sixth Day of February, 2019

Andrei Iancu
*Director of the United States Patent and Trademark Office*